US009023182B1

(12) United States Patent
Cooper

(10) Patent No.: US 9,023,182 B1
(45) Date of Patent: May 5, 2015

(54) SIMPLIFIED PRODUCTION OF ORGANIC COMPOUNDS CONTAINING HIGH ENANTIOMER EXCESSES

(71) Applicant: The United States of America as Represented by the Administrator of the National Aeronautics & Space Administration (NASA), Washington, DC (US)

(72) Inventor: George W. Cooper, Milpitas, CA (US)

(73) Assignee: The United States of America as Represented by the Administrator of the National Aeronautics and Space Administration (NASA), Washington, DC (US)

( * ) Notice: Subject to any disclaimer, the term of this patent is extended or adjusted under 35 U.S.C. 154(b) by 0 days.

(21) Appl. No.: 14/322,767

(22) Filed: Jul. 2, 2014

(51) Int. Cl.
B01J 19/12 (2006.01)
B01J 19/08 (2006.01)

(52) U.S. Cl.
CPC ............ *B01J 19/082* (2013.01); *B01J 19/087* (2013.01); *B01J 19/123* (2013.01); *B01J 19/127* (2013.01)

(58) Field of Classification Search
CPC ...... B01J 19/082; B01J 19/087; B01J 19/123; B01J 19/127
USPC .................. 204/155, 157.68, 157.82, 157.87, 204/157.89
See application file for complete search history.

(56) References Cited

U.S. PATENT DOCUMENTS 4,448,657 A * 5/1984 Turro ............................ 204/155
6,632,332 B1 * 10/2003 Takaki .......................... 204/155
7,258,236 B2 * 8/2007 Raval .............................. 209/8

OTHER PUBLICATIONS

Teutsch et al, "Asymmetric photoreactions as a model for evolution of chirality," Origins of Life and Evolution of the Biosphere, vol. 16, Issue 3-4, p. 420 (1986).*
Li et al, "Magnetoswitchable controlled photocatalytic system using ferromagnetic Fe0 doped titania nanorods photocatalysts with enhanced photoactivity," Separation and Purification Technology vol. 66 (2009), pp. 171-176.*
Feringa et al, "Absolute Asymmetric Synthesis: The Origin, Control, and Amplification of Chirality," Angew. Chem. INt. Ed. 1999, vol. 38, pp. 3418-3438.*
Shigemasa et al, "Formose Reactions. II. The Photochemical Formose Reaction," Bull. Chem. Soc. Japan, vol. 50 (1), pp. 222-226 (1977).*
Simonov et al, "Possible prebiotic synthesis of monosaccharides from formaldehyde in presence of phosphates," Advances in Space Research 40 (2007) pp. 1634-1640.*
Pestunova et al, "Putative mechanism of the sugar formation on prebiotic Earth initiated by UV-radiation," Advances in Space Research 36 (2005) pp. 214-219.*

(Continued)

*Primary Examiner* — Colleen M Raphael
(74) *Attorney, Agent, or Firm* — Christopher J. Menke; Robert M. Padilla

(57) ABSTRACT

The present invention is directed to a method for making an enantiomeric organic compound having a high amount of enantiomer excesses including the steps of a) providing an aqueous solution including an initial reactant and a catalyst; and b) subjecting said aqueous solution simultaneously to a magnetic field and photolysis radiation such that said photolysis radiation produces light rays that run substantially parallel or anti-parallel to the magnetic field passing through said aqueous solution, wherein said catalyst reacts with said initial reactant to form the enantiomeric organic compound having a high amount of enantiomer excesses.

16 Claims, 4 Drawing Sheets

(56) References Cited

OTHER PUBLICATIONS

Jorissen et al, "Asymmetric photoreactions as the origin of biomolecular homochirality: a critical review," Origins of Life and Evolution of the Biosphere vol. 32, pp. 129-142 (2002).*

Bielski et al, "Why is Ribose the Sugar Component of Nucleic Acids? New Insights into Absolute Asymmetric Synthesis and Absolute Enantioselective Separation,".*

Peruvhkin et al, "Influence of the magnetic field upon the low-temperature photolysis of aldehyde, All-Union Conference Polarization of Nuclei and Electrons, and Effects of a Magnetic Field in the Chemical Reactions," USSR's Acad. of Sciences, Siberian Dept. Inst. for Chem. Kinetics and Combustion, Novosibirsk, Apr. 23-25, 1975, sec. 4, p. 40.*

English-language translation of Peruvkhin et al.*

Evans, M.W., "On the symmetry and molecular dynamical origin of magneto chiral dichroism: "Spin chiral dichroism" in absolute asymmetric synthesis," Chem. Phys. Lett. vol. 152, No. 1, Nov. 4, 1988, pp. 33-38.*

Hata, Norisuke, "Photochemical reaction of 4-methyl-2-quinolinecarbonitrile with optically active (S)- or (R)-2-phenylpropionic acid. The magnetic-field and solvent effects and chiral-symmetry breaking," Chem. Phys. vol. 162 (1992) pp. 47-52.*

Popa, Radu, "A Sequential Scenario for the Origin of Biological Chirality," J. Mol. Evol. (1997) vol. 44, pp. 121-127.*

Rikken et al, "Magnetochiral anisotropy," Molecular Physics, 2002, vol. 100, No. 8, pp. 1155-1160.*

\* cited by examiner

US 9,023,182 B1

SIMPLIFIED PRODUCTION OF ORGANIC COMPOUNDS CONTAINING HIGH ENANTIOMER EXCESSES

ORIGIN OF INVENTION

The invention described herein was made by an employee of the United States Government and may be manufactured and used by or for the Government of the United States of America for governmental purposes without the payment of any royalties thereon or therefor.

BACKGROUND OF INVENTION

1. Technical Field of the Invention

The invention is generally directed to a method for making enantiomeric organic compounds having high enantiomer excesses using a magnetic field and photolysis radiation.

2. Description of the Prior Art

All objects, including chemical compounds, have a mirror image. However, some objects cannot be superimposed on their mirror image. For example, a left hand and right hand are not superimposable on each other, e.g. a left hand will not fit into a right hand glove. In the case of chemical compounds, these non-superimposable mirror images are called "enantiomers" and are widely used in biological processes.

Chemical compounds are called "chiral" if their mirror images (enantiomers) cannot be superimposed on each other as described above. Some important chiral biological compounds, e.g., amino acids and sugars, are found exclusively as only one of the two possible enantiomers when used in polymers such as proteins and RNA, respectively. These critical biological polymers cannot work (at least, in today's biology) if both enantiomers are present. Since at least the mid-1800s (Louis Pasteur), scientists have wondered how ancient pre-biological chemistry or life forms started such "homochirality" and how to recreate it in the laboratory starting from smaller non-chiral precursors. For example, how would a chemist synthesize only one mirror image of alanine (a simple amino acid) starting from atoms and smaller molecules that should show no preference towards either of the mirror images? Under normal conditions the synthesis will always produce equal amounts of both: imagine flipping a coin several times—the number of heads and tails will be nearly 50-50. There have been a multitude of attempts to create enantiomer enrichments (or "excesses") in a prebiotic way—both for commercial as well as purely scientific research reasons.

Previous studies of carbonaceous meteorites are relevant to the origin of the present invention as these objects are the oldest (4.6 billion years) in the solar system and therefore their contents are relevant to the study of the first chemical processes. Evidence was found for significant enantiomer excesses in sugar derivatives (sugar acids) in these meteorites: and a natural question was raised about the origin of such a strange phenomenon. (Cooper G., Sant M. and Asiyo C. (2009) Anomalous enantiomer ratios in meteoritic sugar derivatives. Lunar Planet. Sci. Conf. Abs #2537.) Before this work, it was known that some amino acids in meteorites also possessed small enantiomer excesses (Pizzarello S., Cooper G. W. and Flynn G. J. The Nature and Distribution of the Organic Material in Carbonaceous Chondrites and Interplanetary Dust Particles in Meteorites and the Early Solar System II. D. Lauretta, L. A. Leshin, and H. Y. McSween Jr., Eds. University of Arizona Press (2006)). The origin(s) of meteorite enantiomer excesses is still unknown. It is possible that mild photolysis and magnetism may have had a role in the origin of enantiomer excess.

Attempts at using magnetism alone to induce a preference of one enantiomer go back over a century including those by Pasteur to create homochiral molecules in a magnetic field (Mason, S. F., (1984) Origins of Biomolecular Handedness, nature 311: 19-23). To date, there has been no convincing evidence of such a phenomenon (e.g., Bonner, W. A., (1991) The origin and amplification of biomolecular chirality, Origins of Life, 21:59-111; Barron, L. D. (1994) Can a Magnetic Field Induce absolute Asymmetric Synthesis, Science 266, 1491-1492). However, theoretical and experimental studies have suggested or shown that enantiomer selectivity is possible (although extremely small) with the combination of a magnetic field and radiation (light) of parallel, or anti-parallel, direction. Experimental evidence showed that enantiomeric "excess" can be achieved when a pre-made target compound is subjected to a combination of a magnetic field and parallel radiation, see Rikken and Raupach (2000) "Enantioselective mangetochiral photochemistry", Nature 405, 932-935. These workers placed a $K_3Cr(III)$ trix-oxalato complex in very powerful magnetic fields ranging up to approximately 15 Tesla (T) and irradiated it with intense unpolarized light of varying wavelength (approximately 692-701 nm). The complex, which is chiral, then dissociates in an asymmetric fashion, i.e. one enantiomer dissociates slightly more than the other, therefore achieving extremely small "excess" of one of the enantiomers. Maximum excess ($\sim 1.5 \times 10^{-4}$) occurred at 695.5 nm and 15T but excesses were observed at lower field strength; from the graph of their data small excesses might be expected at under 3T.

However, there are major differences between past theoretical and laboratory "magnetochiral" work and the present invention. For one example, the past work conducted by Rikken and Raupach used the test compound $K_3Cr(III)$ tris-oxolato, which is not biologically relevant and was used in its final form (i.e., it was already synthesized), and its absorption (of light) characteristics were previously well defined. Additionally, the excesses created were extremely small ($\sim 1.5 \times 10^{-4}$) and required a laser to measure the difference in abundance of the two enantiomers. The radiation and magnetic field strengths were relatively powerful: the magnetic strength needed for maximum effect (largest enantiomer excesses) was in the range of those used in nuclear magnetic resonance (NMR) while the light source was a laser.

From a scientific point of view, interest in the origins of both homochirality and biologically relevant organic compounds has centered on some of these points: (1) what is the origin(s) of the synthesis of biologically relevant compounds from simpler precursor molecules approximately 3.8 to 4 billion years ago and (2) were there mild (and pre-biotic) methods of producing large enantiomer excesses? It has been known for well over a century that water-formaldehyde solutions easily produce a variety of sugars. The synthesis sequence builds up to at least six-carbon sugars: formaldehyde-a two-carbon compound-three-carbon-four carbon, etc. This reaction, shown in FIG. 1, is known as the "Formose" reaction (Walker J. F. (1964) Formaldehyde. Reinhold Publishing Corp.; Langenbeck W. (1942) Die formaldehydkondensation als organische autokatalyse. Naturwissenschaften 30, 30; Mizuno T. and Weiss A. H. (1974) Synthesis and Utilization of Formose Sugars in Advances in Carbohydrate Chemistry and Biochemistry. Eds. R. Stuart Tipson and Derek Horton, Vol. 29, pp. 173-227, (1974)). Formaldehyde, a one-carbon compound ($CH_2O$) produces these and many other sugars in water solutions. The first compound produced from formaldehyde, the two-carbon compound is called glycoaldehyde and the three-carbon sugar is called glyceraldehyde. The reaction is catalyzed by a base and a divalent metal such as calcium. However, the formose reaction, as with all known non-biological reaction, does not produce compounds containing enantiomer excesses (Mizuno and Weiss, 1974).

Currently, chemical companies do sell some pure enantiomers, however, to attain such enrichments the synthesis ultimately begins from a biological source. In addition to being a time-consuming process, this usually makes the price of enantiomers higher than that of a corresponding non-chiral compound that can sometimes be produced from abiotic (non-biological) synthesis. This can be especially true of the rare (non-biological) enantiomer, which can cost several times more than the common biological enantiomer, if it is made at all.

For over 160 years scientists have attempted to produce abiotic enantiomer excesses in organic compounds. In addition to commercial reasons, scientists want a more plausible explanation of how "homochirality" could have begun in life forms in the Earth's history.

SUMMARY OF THE INVENTION

The present invention is directed to a method for generating enantiomeric organic compounds by combining the use of mild photolysis radiation and magnetism to produce enantiomer excesses. The present invention differs over the prior art in a number of ways. First, the present invention does not use "pre-made" compounds, but is directed to the synthesis of the enantiomeric organic compounds. Second, the present invention uses relatively mild and generally accessible physical conditions. Third, the present invention is capable of producing biologically useful compounds. And finally, the present invention generates large enantiomer excesses that are easily measured with common laboratory equipment. In a preferred embodiment, the enantiomer excesses are at least 50% and may be as high as 100% (i.e. homochirality). The overall cost of the method used in the present invention should be much less than current methods of enantiomer production.

As described below, the present invention preferably combines a formose-type reaction with physical forces to produce desired enantiomer excesses.

The present invention is directed to a simplified method for producing enantiomer excesses from simple and relatively inexpensive initial compounds, e.g. formaldehyde and simple salts, and hardware components without the need and expense of using, at some stage, biological sources. This should result in significant savings in the production of single enantiomers of sugar and sugar acids for business as well as for research in general.

The present invention is directed to the production of chiral organic compounds, such as sugars, sugar acids and possibly amino acids, which are enriched in one of the two possible enantiomers of individual compounds. It also allows the enrichment of the other enantiomer by simply reversing the applied physical conditions. Unlike the commercial production of most rare enantiomers, the present invention employs conditions that are extremely common, non-biological and relatively inexpensive to set up. The apparatus needed for the syntheses can be purchased from several commercial sources and the enrichments can be produced in a matter of hours.

The present invention differs from the prior art in that it creates excesses during synthesis of compounds from simple and inexpensive initial compounds, i.e. precursors. Additionally, the present invention provides excesses of the enantiomers in the range of 7:1 or more. These excesses can be measured with a common gas chromatograph-mass spectrometer but can also be measured with a polarimeter. The excesses in the present invention are permanent and the enantiomeric organic compounds can be removed and isolated for any desired research or commercial purpose. The magnetic field strength is mild, preferably ranging from about 0.16 to ~0.3T, and judging from some of the large excesses, lower magnetic strength could also be used. Commercially produced magnets, such as neodymium magnets, may be used to obtain the field strength.

BRIEF DESCRIPTION OF THE DRAWINGS

The features and advantages of the present invention will become apparent from the following detailed description of a preferred embodiment thereof, taken in conjunction with the accompanying drawings, in which.

DETAILED DESCRIPTION OF THE INVENTION

The present invention is directed to a method for making an enantiomeric organic compound having a high amount of enantiomer excesses. The method includes the steps of a) providing an aqueous solution including an initial reactant and a catalyst; and b) subjecting said aqueous solution simultaneously to a magnetic field and photolysis radiation such that said photolysis radiation produces light rays that run substantially parallel or anti-parallel to the magnetic field passing through said aqueous solution, wherein said catalyst reacts with said initial reactant to form the enantiomeric organic compound having a high amount of enantiomer excess. In a preferred embodiment, the majority of the resulting enantiomeric organic compounds have high amounts of enantiomer excesses of at least 48% to nearly homochiral. It is understood that the terms "parallel" and "anti-parallel" are not absolute and some degree of off-set from parallel, such as ±10 degrees, is still within the term "substantially parallel or anti-parallel". In a first embodiment, the initial reactant is formaldehyde that reacts using the known Formose reaction that is catalyzed by a base and a divalent metal such as calcium or magnesium. In one preferred embodiment, the magnetic field strengths range from 0.16-0.3 Tesla and photolysis radiation at wavelengths near the UV-visible end of solar, preferably ~365-400 nm. In a first embodiment, the generated enantiomeric organic compounds are sugars and/or sugar acids. In a second embodiment, the generated enantiomeric organic compound is an amino acid. However, it is contemplated that other enantiomeric organic compounds may be formed with D/L excesses using the present invention relying on the magnetic field and photolysis as disclosed herein.

Figure 1:
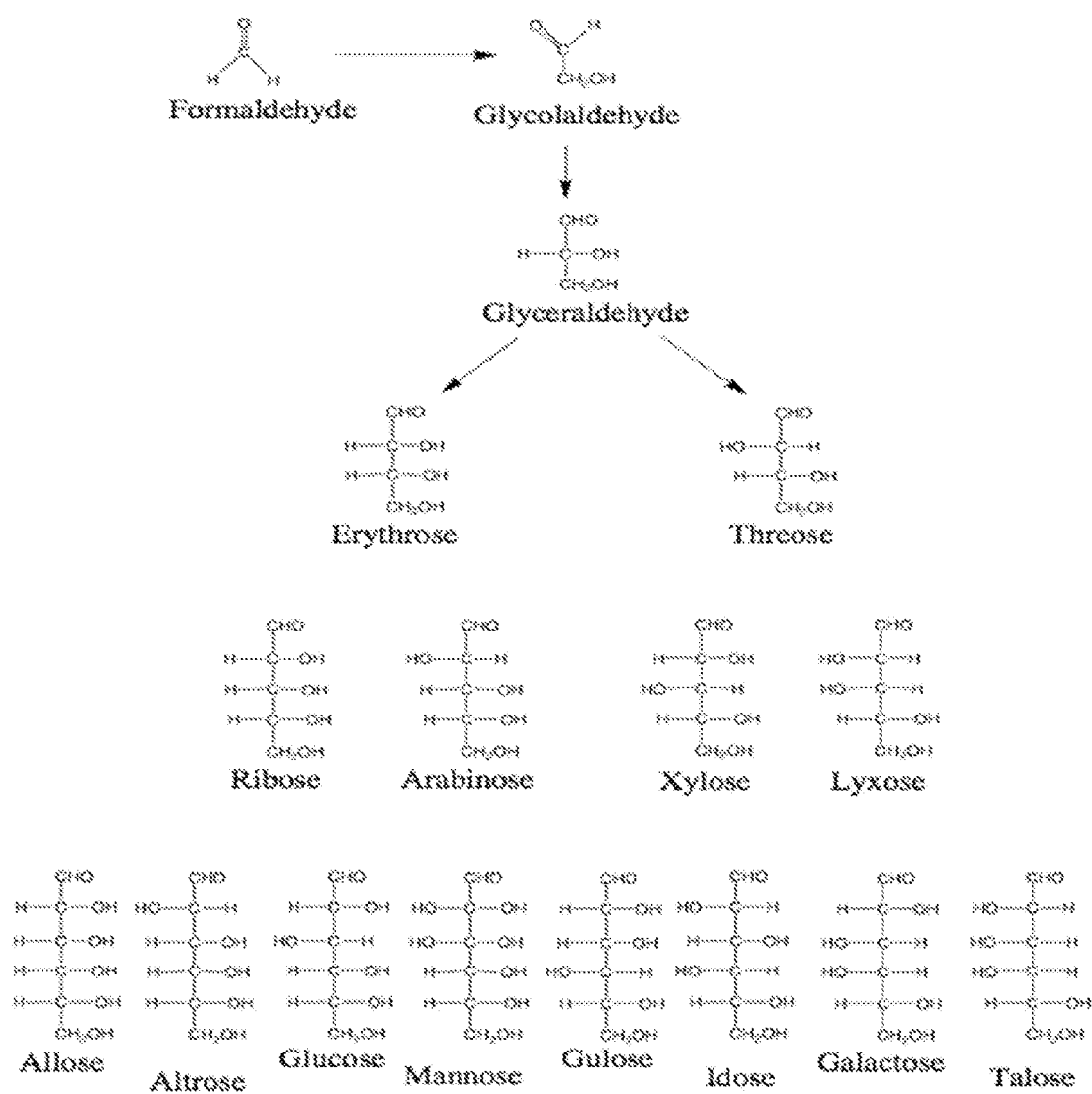
FIG. 1 shows the structural relationships of sugars starting with the smallest three-carbon sugar, glyceraldehyde.

In one embodiment of the present invention, the initial reactant is a small high-energy molecule such as formaldehyde ($CH_2O$) that continuously reacts with itself in an aqueous solution to build larger molecules (see FIG. 1). A magnetic field and photolysis radiation may be used as the asymmetric cause of enantiomer excesses. Formaldehyde and glycolaldehyde are included to illustrate the build up of carbon chains during progression of the formose reaction. However, many more compounds are also known to form in formose reactions.

The following Examples are used to illustrate the beneficial results that are obtained using the present method. However, it should be understood by one of ordinary skill in the art that the method may be modified from these preferred embodiments without departing from the scope of the present invention.

Experiment

Figure 2:
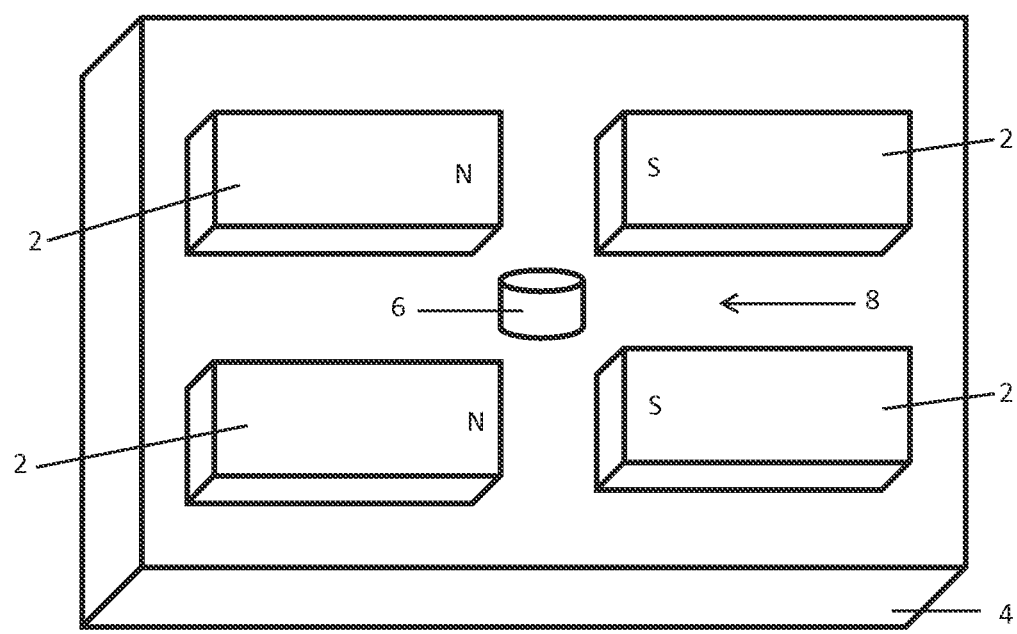
FIG. 2 shows one embodiment of an apparatus used to produce the enantiomer excess in accordance with the present invention.

Four neodymium magnets 2 were locked in a specially built aluminum holder 4 with a photolysis radiation light source 8, as seen in FIG. 2. Each pair of magnets 2 is aligned from the north to south pole. The photolysis radiation light source 8 consists of a simple lamp fitted with a 100-watt mercury bulb (from Sylvania) that produces light of wavelength near the UV end of solar (365 nm) in steps to 576 nm depending on the filter used. To date, most experiments have been done at 365 nm including those described herein. It can be seen that the photolysis radiation light rays will be substantially parallel (or anti-parallel) to the magnetic field. A preliminary analysis utilizing only one magnet indicates that enantiomer excesses are also possible with this method: this should be expected because the reaction still takes place in a magnetic field.

Sample Preparation:

The sample mixture was placed in a quartz sample tube 6 at the indicated position: the actual tube is longer than illustrated in FIG. 2 but the sample volume is within the magnetic field. Typical formaldehyde (paraformaldehyde) concentrations have been 0.1-1.0M with total volumes of approximately 1-2 milliliters (mL). Calcium hydroxide, $Ca(OH)_2$, is long known to be an effective catalyst for formose reactions (Walker, 1964; Mizuno and Weiss, 1974). However, due to the nearly insoluble nature of $Ca(OH)_2$, a common method of generating $Ca(OH)_2$ in the reaction mixture was employed in several runs. Two water-soluble compounds, sodium hydroxide (NaOH) and calcium chloride ($CaCl_2$) in 2:1 molar proportion are added to the mixture: these two compounds react to form $Ca(OH)_2$ during the formose reaction. Calcium carbonate ($CaCO_3$) is much less used as a catalyst in formose reactions (Mizuno and Weiss, 1974). It was tried as a catalyst and found to also yield good results (e.g., FIG. 3, A, B). However, $CaCO_3$ is also insoluble and was also generated with soluble compounds, sodium carbonate ($Na_2CO_3$) and calcium chloride ($CaCl_2$). Typical conditions: paraformaldehyde, 0.1 to 0.3M; $Na_2CO_3$, 0.1M; $CaCl_2$, 0.1M. Following the same general procedure, magnesium also gives high enantiomer excesses. A volume of water is added separately to bring the total reaction volume to the desired level. In most cases the reactions have been done at room temperature. When initial warming was desired (to dissolve the paraformaldehyde more quickly) the water is heated alone from the other components and added last (the other components are already in the sample holder in the magnetic and light fields) to assure that the paraformaldehyde dissolves and that the reaction does not progress before magnetism+light can effect the formation of any enantiomer excesses. If the reaction proceeds too far before being subjected to the magnetic/light field a racemic mixture where all enantiomers are produced equally will result (e.g. FIG. 3A). In cases where hot water was added (initially), most samples were then allowed to cool and react further at ambient temperature (room temperature at 22° C.). Samples have been irradiated from slightly less than one hour to approximately fifty hours.

Figure 3A:
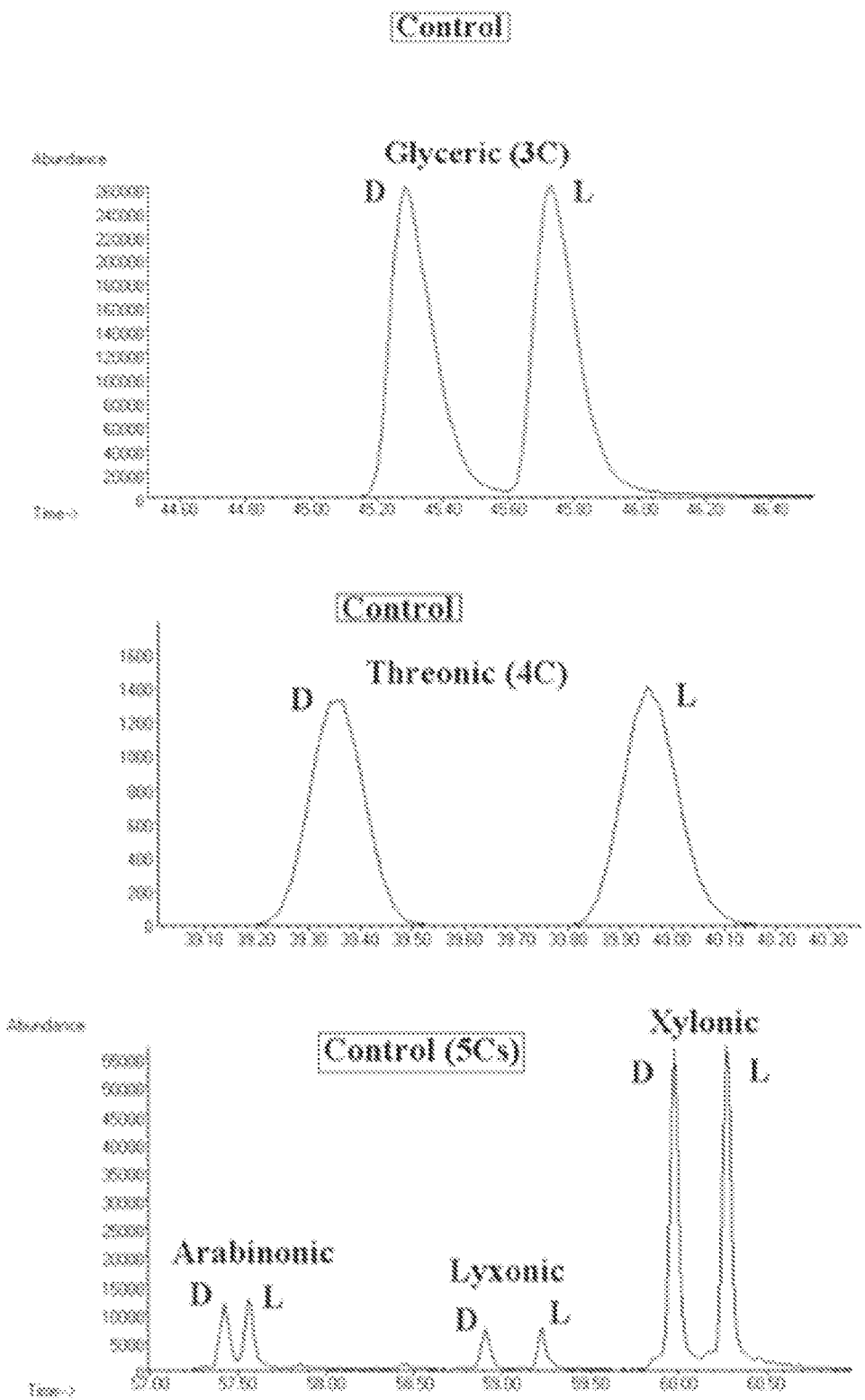
FIG. 3A shows control reactions: formaldehyde+water+salts and either photolysis (light) with no source of magnetism, or vice versa, or neither of the physical forces.
Figure 3B:
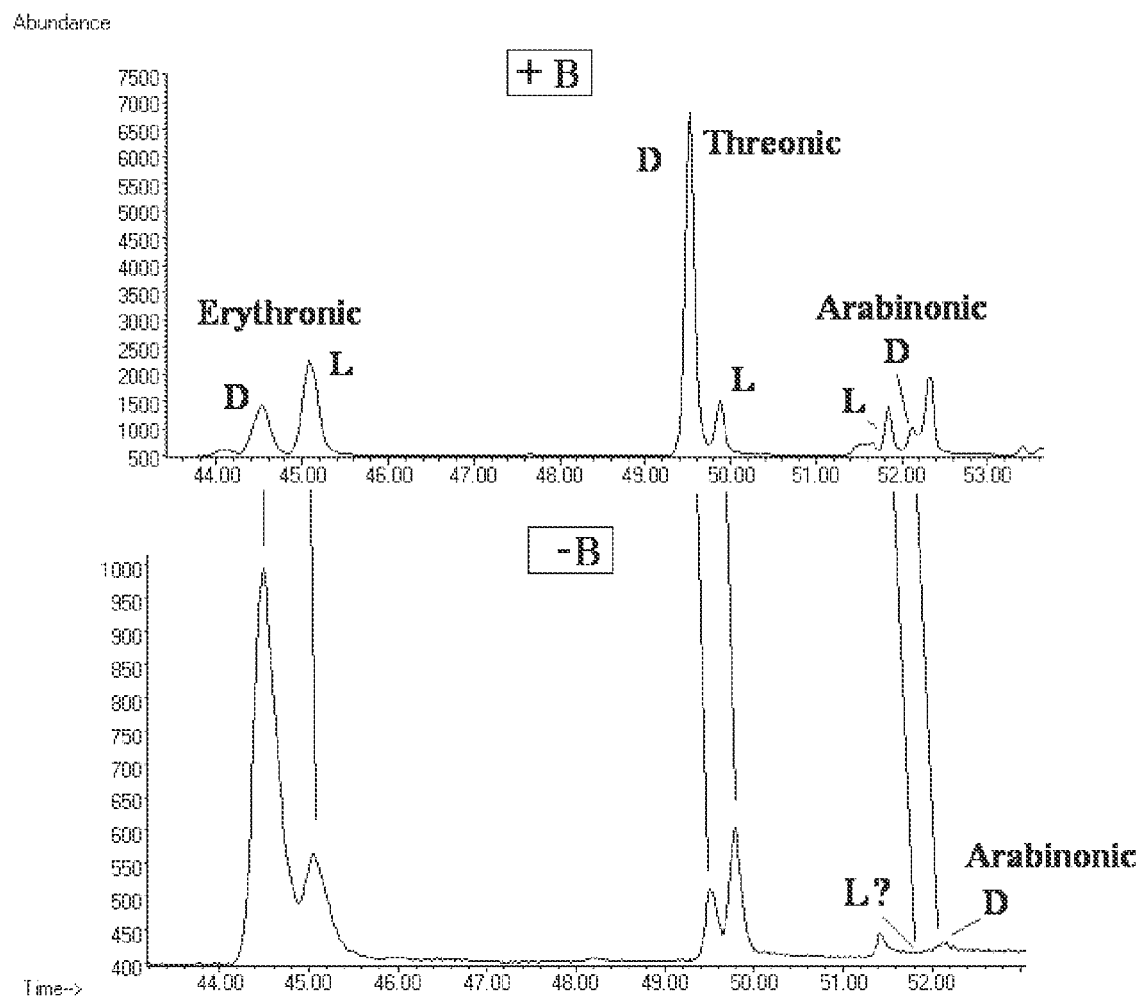
FIG. 3B shows the combined effects of photolysis radiation and magnetism: enantiomer excesses are produced in individual compounds and can be reversed depending on the direction of the magnetic field.

Results:

Data showing significant asymmetric effects is provided in FIG. 3. FIG. 3A shows control reactions: formaldehyde+water+salts and either photolysis (light) with no source of magnetism, or vice versa, or neither of the physical forces. It is seen that compounds are produced in the expected 50:50 ratios, i.e., they are produced in racemic amounts. Each enantiomer is commonly labeled as "D" or "L". FIG. 3B (top panel) shows the results with the same chemical conditions but with the sample in a magnetic field of 3,000 gauss (10,000 gauss=1 Tesla (T)); photolysis is from south (S) to north (N). FIG. 3B (bottom panel) is simply a reversal in the direction of magnetism: reversing the direction of photolysis achieves the same results. Samples in FIG. 3B were irradiated approximately 45 hours however excesses can be produced in three hours and possibly less. The control in FIG. 3A, where xylonic (i.e., xylose) is racemic, is the norm as shown by over a hundred years of formose reactions, or any normal non-chiral synthesis (other control compounds are not shown in FIG. 3A but are also racemic). As shown in FIG. 3B the D and L is in excess depending on the orientation of the magnetic field, or equivalently, the direction of light. The sugars in some cases were converted to their slightly oxidized form (sugar acids) to simplify the identification of enantiomers. The compounds shown in FIG. 3 are sugar acids: the sugars produced in the reactions were converted to sugar acids (e.g., from threose to threonic acid, xylose to xylonic, etc.) for the ease of analysis. For example, just one sugar may produce as many as eight to ten peaks on a (chiral) chromatogram due to its multiple forms (isomers) while the corresponding sugar acid only produces two (the D and L) peaks: however, the D/L ratio of the acid accurately represents the D/L ratio of each corresponding original sugar. FIG. 3B contains predominately four-carbon (4C) acids, erythronic and threonic acid. However, in this specific case, they represent a summation of the D/L ratios of the many higher sugars (5 and 6C) produce in the experiments. The deliberately chosen oxidation conditions (including peroxide) cleaved and oxidized the higher sugar to the 4C acids. Again, this allowed for easier analysis but it also gives a summary of the bulk enantiomer excesses produced in the experiments on one chromatogram. Depending on structure (see FIG. 1), some compounds cleave and oxidized to erythronic acid and others to threonic acid.

These Experiments illustrate an additional benefit of the current invention from a research or commercial point of view. At least two classes of enriched enantiomers can potentially be produced from one reaction run—sugars and, by slight oxidation, sugar acids. As mentioned above, the enantiomer excesses shown in FIG. 3B represent the combined excesses of many of the produced compounds. Using a proven and gentler method of oxidation (bromine), the individual sugar acids representing only their parent sugar can be analyzed. Presently the enantiomer excesses of individual sugars are being quantified. For example, individual anomers (isomers) of arabinose show the following: one of the six-membered ring (pyranose) anomers contains a D excess of approximately 48%. However, one furanose anomer (five-membered ring) contains an L excess of ~78% and in the second pyranose anomer, none of the D enantiomer could be identified (at the limit of detection). Generally pyranoses are more abundant at equilibrium—the second furanose could not be definitively identified.

Sugar alcohols (in the same runs) are also targets of D/L analysis but their enantiomer ratios will be analyzed after the sugars/sugar acids. The reaction conditions are continuously updated in attempts to achieve higher enantiomer excess. On completion of a reaction, individual anomers could be purified to the desired degree by common methods. Currently, liquid chromatography is the most common method for bulk purification of sugars.

Although the present invention has been disclosed in terms of a preferred embodiment, it will be understood that numerous additional modifications and variations could be made thereto without departing from the scope of the invention as defined by the following claims:

We claim:

1. A method for making an enantiomeric organic compound having an amount of enantiomer excesses comprises:
    a) providing an aqueous solution including an initial reactant and a catalyst; and
    b) subjecting said aqueous solution simultaneously to a magnetic field and photolysis radiation such that said photolysis radiation produces light rays that run substantially parallel or anti-parallel to the magnetic field passing through said aqueous solution, wherein said catalyst reacts with said initial reactant to generate the enantiomeric organic compound having an amount of enantiomer excesses,
    wherein said initial reactant is formaldehyde.

2. The method of claim 1 wherein said catalyst is selected from the group consisting of calcium hydroxide, calcium carbonate, magnesium carbonate, and sodium carbonate.

3. The method of claim 1 wherein said magnetic field is generated at about 0.16-0.3 Tesla.

4. The method of claim 1 wherein said photolysis radiation is provided at a wavelength near the UV-visible end of the electromagnetic spectrum.

5. The method of claim 1 wherein said photolysis radiation is provided at a wavelength near ~365-400 nm.

6. The method of claim 1 wherein said generated enantiomeric organic compound is a sugar or a sugar acid.

7. The method of claim 1 wherein said generated enantiomeric organic compound is an amino acid.

8. The method of claim 1 wherein the generated enantiomeric organic compound is used for commercial or research purposes.

9. The method of claim 1 wherein the generated enantiomeric organic compound is generated via a formose-type reaction.

10. The method of claim 1, wherein said amount of enantiomer excesses are at least 48%.

11. A method for making an enantiomeric organic compound having an amount of enantiomer excesses comprises:
    a) providing an aqueous solution including an initial reactant and a catalyst; and
    b) subjecting said aqueous solution simultaneously to a 0.16-0.3 Tesla magnetic field and photolysis radiation such that said photolysis radiation produces light rays at a wavelength near ~365-400 nm that run substantially parallel or anti-parallel to the magnetic field passing through sais aqueous solution, wherein said catalyst reacts with said initial reactant to generate the enantiomeric organic compound having an amount of enantiomer excesses of at least 48%,
    wherein said initial reactant is formaldehyde.

12. The method of claim 11 wherein said catalyst is selected from the group consisting of calcium hydroxide, calcium carbonate, magnesium carbonate, and sodium carbonate.

13. The method of claim 11 wherein said generated enantiomeric organic compound is a sugar or a sugar acid.

14. The method of claim 11 wherein said generated enantiomeric organic compound is an amino acid.

15. The method of claim 11 wherein the generated enantiomeric organic compound is used for commercial or research purposes.

16. The method of claim 11 wherein the generated enantiomeric organic compound is generated via a formose-type reaction.

* * * * *